United States Patent [19]

Horacek

[11] Patent Number: 5,373,038

[45] Date of Patent: Dec. 13, 1994

[54] FLAME RESISTANT PLASTICS CONTAINING GUANIDINE BARBITURATES OR GUANIDINE THIOBARBITURATES, AND ALSO GUANIDINE BARBITURATES AND GUANIDINE THIOBARBITURATE

[75] Inventor: Heinrich Horacek, Puchenau, Austria

[73] Assignee: Chemie Linz Gesellschaft m.b.H., Austria

[21] Appl. No.: 49,437

[22] Filed: Apr. 20, 1993

[30] Foreign Application Priority Data

Apr. 27, 1992 [AT] Austria ................ A863/92

[51] Int. Cl.$^5$ ............................................ C08K 5/3492
[52] U.S. Cl. ................................. 524/100; 544/301
[58] Field of Search ..................... 544/301; 524/100

[56] References Cited

U.S. PATENT DOCUMENTS

| | | | |
|---|---|---|---|
| 2,078,323 | 4/1937 | Gebauer | 544/301 |
| 2,932,643 | 4/1960 | Zaugg et al. | 544/304 |
| 3,888,822 | 6/1975 | Gilleo et al. | 524/100 |
| 4,298,518 | 11/1981 | Ohmura et al. | 524/100 |
| 4,670,441 | 6/1987 | Kühne et al. | 544/301 |
| 5,147,914 | 9/1992 | Horacek | 524/185 |

FOREIGN PATENT DOCUMENTS

| | | |
|---|---|---|
| 044424 | 1/1982 | European Pat. Off. . |
| 461612 | 12/1991 | European Pat. Off. . |
| 2222375 | 10/1974 | France . |

OTHER PUBLICATIONS

Siebourg et al., Chem. Abstracts 96:200815p (1982).
Anatol et al., Chem. Abstracts 82:171030g (1975).

*Primary Examiner*—Kriellion S. Morgan
*Attorney, Agent, or Firm*—Wenderoth, Lind & Ponack

[57] ABSTRACT

Flame resistant plastics that contain guanidine barbiturates, guanidine thiobarbiturates or their mixtures as flame retardants, and also guanidine barbiturate and guanidine thiobarbiturate.

9 Claims, No Drawings

FLAME RESISTANT PLASTICS CONTAINING GUANIDINE BARBITURATES OR GUANIDINE THIOBARBITURATES, AND ALSO GUANIDINE BARBITURATES AND GUANIDINE THIOBARBITURATE

The present invention relates to plastics that contain guanidine barbiturates or guanidine thiobarbiturates in order to improve their flame resistance, to a process for improving the flame resistance of plastics by adding guanidine barbiturates or guanidine thiobarbiturates, and also to guanidine barbiturate and guanidine thiobarbiturate.

Although the halogen-containing flame retardants normally used exhibit a good action, they suffer from the serious disadvantage that in the event of a fire, especially in the event of a prolonged fire, they release toxic and corrosive chlorine and bromine compounds. Halogen-free flameproofing agents, for example melamine or melamine cyanurate (U.S. Pat. No. 4,298,518), have been used to obviate these disadvantages.

Melamine has, inter alia, the disadvantage that it tends to bloom when the plastics are processed, which means that in some cases it migrates to the surface and leaves an objectionable film for example in injection molds. Melamine cyanurate tends to sublime on incorporation into the plastic, the latter foaming somewhat and the bulk density being reduced. It is an object of the present invention to provide novel substances that are suitable as flame retardants for plastics. We have surprisingly found that guanidine barbiturates and guanidine thiobarbiturates have a good flame retardant action on plastics.

The present invention accordingly relates to flame resistant plastics that contain guanidine barbiturates or guanidine thiobarbiturates or their mixtures as flame retardants. The invention also relates to a process for enhancing the flame resistance of plastics, in which guanidine barbiturates or guanidine thiobarbiturates or their mixtures are added as flame retardants to the plastics or their precursors.

Guanidine barbiturates and guanidine thiobarbiturates may be obtained by reacting guanidine or its salts with barbituric acid, thiobarbituric acid or its derivatives. Derivatives of barbituric acid and thiobarbituric acid for the purposes of the present invention are in particular compounds of the formula

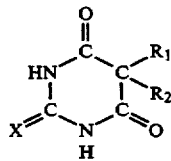

in which R1 and R2 are, independently of one another, H, alkyl or aryl radicals, and X is O or S. These compounds can be obtained for example by reacting the suitably substituted malonic esters with urea or thiourea. They are also commercially available. Derivatives of barbituric acid are described for example in Advances in Heterocyclic Chemistry, Academic Press, New York 1985, Vol. 38, pages 229–241.

The reaction of barbituric acid, thiobarbituric acid or their derivatives with guanidine or its salts preferably takes place in an aqueous medium, the sparingly soluble, substituted or unsubstituted guanidine barbiturates or guanidine thiobarbiturates precipitating out. The latter are then separated off, washed and dried. Preferably, 1 mol of guanidine or 1 equivalent of guanidine salts, for example ½ mol of guanidine carbonate, is reacted with 1 mol of barbituric acid, thiobarbituric acid or their derivatives. Substituted guanidine barbiturates and guanidine thiobarbiturates, which are used as pharmaceuticals, are described for example in U.S. Pat. No. 2,932,643.

The present invention also relates to the novel compounds guanidine barbiturate and guanidine thiobarbiturate. These compounds are prepared for example by reacting unsubstituted barbituric acid or thiobarbituric acid with guanidine or its salts. Guanidine barbiturate has a melting point of 274°–278° C., it decomposes at 430° C., and the solubility in water is 0.2 g/l (20° C.). The melting point of guanidine thiobarbiturate is 320°–325° C., the decomposition temperature is above 450° C., and the solubility in water is 0.1 g/l (20° C.).

According to the invention guanidine barbiturates and guanidine thiobarbiturates are suitable as flame retardants for thermoplastics and also for thermosetting or elastomeric plastics. Suitable plastics are for example those from the group of the polyolefins, for example polyethylene, polypropylene or ethylene-propylene copolymers, polybutylene or polymethylpentene, polyvinyl acetate, polyamides, polyacrylonitrile or polyacrylonitrile-containing plastics, for example ABS (acrylonitrile-butadiene-styrene) copolymers or SAN (styrene-acrylonitrile) copolymers, thermoplastic or crosslinked polyurethanes, thermoplastic, unsaturated or crosslinked polyesters, epoxides, acrylic resins, urea-formaldehyde, melamine-formaldehyde or phenol-formaldehyde resins. The plastics may also be expanded. It is also possible to render mixtures of various plastics or copolymers from various monomers, for example ethylene-propylene copolymers, flame retardant with guanidine barbiturates or guanidine thiobarbiturates. Guanidine barbiturates and guanidine thiobarbiturates have proved particularly useful flame retardants for nitrogen-containing plastics, for example polyamides, polyurethanes, polyacrylonitrile or polyacrylonitrile-containing plastics.

In addition to their good flame-retarding action, guanidine barbiturates and guanidine thiobarbiturates have the additional advantage that they are sparingly soluble in water.

According to the invention guanidine barbiturates and guanidine thiobarbiturates may be used as such or together with other flame retardants. Further suitable flame retardants are preferably halogen-free retardants, for example melamine, melamine cyanurate, phosphorus-based flame retardants, for example ammonium polyphosphate, phosphoric esters and red phosphorus, or flame retardants based on boric esters.

The preparation of the flame resistant plastics is carried out for example by mixing guanidine barbiturates or guanidine thiobarbiturates or their mixtures with the relevant plastics. In the case of thermoplastics the mixture can then be melted for example in an extruder. In the case of resins it is also possible to add guanidine barbiturates and guanidine thiobarbiturates to the precursors of the plastic during the course of the formation of the latter.

For example, in the case of polyurethanes it is possible to add guanidine barbiturates and/or guanidine thiobarbiturates and also, if desired, further flame retardants to the polyols or to the polyisocyanates before the polymerization reaction.

In order to render the plastics flame retardant, preference is given to the use of guanidine barbiturates or guanidine thiobarbiturates in which at least 95% by weight have a maximum grain size of 0.025 mm. The content of guanidine barbiturates or guanidine thiobarbiturates in the plastic is generally from about 1 to 30% by weight, preferably from about 5 to 20% by weight, depending on the relevant flame resistance requirements.

In the Examples below the following plastics were rendered flame retardant:

PA 6 Nylon 6 (Ultramid B4, BASF)
PA 6,6 Nylon 6,6 (Durethane A31, Bayer)
TPU Thermoplastic polyurethane (Desmopan Shore AS80, Bayer)
ABS Acrylonitrile-butadiene-styrene copolymer (Terluran 99S, BASF)
SAN Styrene-acrylonitrile copolymer (Luran 53, BASF)
PP Polypropylene (Daplen PP CS10, Petrochemie Danubia)
PET Polyethylene terephthalate (Arnite D02300, Akzo)
PBT Polybutylene terephthalate (Arnite T06200, Akzo)

EXAMPLE 1

Preparation of guanidine barbiturate 600 g of water and 384 g (3 mol) of barbituric acid (Merck) were heated to 90° C. and 270 g (1.5 mol) of guanidine carbonate (Chemie Linz) were added while stirring. After stirring for a further 2 hours at the boiling point while refluxing, the guanidine barbiturate formed was suction filtered, washed twice with cold water, and dried overnight at 105° C. in a drying cabinet. Guanidine barbiturate was obtained in a yield of 75%. The melting point was 274°–278° C., and the decomposition temperature was 430° C. The compound was identified by means of its IR spectrum.

|  | Elemental analysis: | | | |
|---|---|---|---|---|
|  | C | H | N | O |
| Calculated | 32.1% | 4.8% | 37.4% | 25.7% |
| Found | 31.5% | 4.9% | 36.4% | 26.0% |

EXAMPLE 2

Preparation of guanidine thiobarbiturate 600 g of water and 432 g (3 mol) of thiobarbituric acid (Merck) were heated to 90° C. and 270 g (1.5 mol) of guanidine carbonate (Chemie Linz) were added while stirring. After stirring for a further 2 hours at the boiling point while refluxing, the guanidine thiobarbiturate formed was suction filtered, washed twice with cold water, and dried overnight at 105° C. in a drying cabinet. Guanidine thiobarbiturate was obtained in a yield of 80%. The melting point was 320°–325° C., and the decomposition temperature was above 450° C. The compound was identified by means of its IR spectrum.

|  | Elemental analysis: | | | | |
|---|---|---|---|---|---|
|  | C | H | N | O | S |
| Calculated | 29.5% | 4.4% | 34.5% | 15.8% | 15.8 |
| Found | 29.2% | 4.5% | 33.8% | 16.0% | 16.5% |

EXAMPLE 3

5 kg/hour of PA 6 and 0.32 kg/hour of guanidine barbiturate were metered separately to a twin-screw extruder (LSM 30/34 GL 9R, Leistritz), melted at 270° C. and homogenized, extruded through a 2 mm perforated die and granulated by chopping. The granules were then press molded in a hot press at 280° C. into 3.2 mm thick platelets, which were tested according to UL 94 as regards their flame resistance. The flame resistance was classed as V-0, corresponding to a maximum continuation of burning of 10 seconds after application of the test flame for 10 seconds.

EXAMPLES 4–16

Test platelets of plastics granules rendered flame resistant with guanidine barbiturate (GB) or guanidine thiobarbiturate (GTB) were prepared in a manner similar to Example 3, except that the plastics and amounts (% by weight) of guanidine barbiturate or guanidine thiobarbiturate specified in Table 1 were employed. In Example 9 ammonium polyphosphate (Exolit 422, Hoechst) was used as a further flame retardant in addition to guanidine barbiturate. The flame resistance corresponded in all cases to fire class V-0.

Comparative Example V1

Test platelets of PA6 without flame retardant were prepared in a similar manner to Example 2. The flame resistance corresponded to fire class V-2 according to UL 94, corresponding to a continuation of burning of 30 seconds, flaming particles in addition dripping from the specimen.

Comparative Example V2

Test platelets of PA6 with an addition of 8% by weight of melamine cyanurate (Chemie Linz) as flame retardant were prepared in a similar manner to Example 2. The flame resistance corresponded to fire class V-0 according to UL 94. The bulk weight of the granules was 620 g/l (Table 1) and was thus less than that of the plastics containing guanidine barbiturate or guanidine thiobarbiturate.

TABLE 1

|  | Plastic | Flame retardant* | % by wt. | Fire class (UL 94) | Bulk density of the granules (g/l) |
|---|---|---|---|---|---|
| 3 | PA 6 | GB | 6 | V-0 | 700 |
| 4 | PA 66 | GB | 6 | V-0 | 800 |
| 5 | TPU | GB | 10 | V-0 | 750 |
| 6 | ABS | GB | 20 | V-0 | 720 |
| 7 | SAN | GB | 20 | V-0 | 760 |
| 8 | PP | GB | 25 | V-0 | 720 |
| 9 | PP | GB | 12.5 | | |
|  |  | Phosph | 12.5 | V-0 | 680 |
| 10 | PA 6 | GTB | 6 | V-0 | 710 |
| 11 | PA 66 | GTB | 6 | V-0 | 760 |
| 12 | TPU | GTB | 10 | V-0 | 720 |
| 13 | PET | GTB | 20 | V-0 | 780 |
| 14 | PBT | GTB + GB | 10 + 10 | V-0 | 750 |
| 15 | ABS | GTB | 25 | V-0 | 720 |
| 16 | SAN | GTB | 20 | V-0 | 690 |
| V1 | PA 6 | — | — | V-2 | 620 |

TABLE 1-continued

| Plastic | Flame retardant* | % by wt. | Fire class (UL 94) | Bulk density of the granules (g/l) |
|---|---|---|---|---|
| V2 PA 6 | MC | 8 | V-0 | 620 |

*GB  Guanidine barbiturate
GTB  Guanidine thiobarbiturate
MC  Melamine cyanurate
Phosph  Ammonium polyphosphate

What I claim is:

1. A flame resistant plastic that contains guanidine barbiturates or guanidine thiobarbiturates or their mixtures as flame retardant.

2. The flame resistant plastic as claimed in claim 1, which contains nitrogen in the polymer chain.

3. The flame resistant plastic as claimed in claim 1, which comprises polyamides, polyurethanes, polyacrylonitrile or polyacrylonitrile-containing plastics.

4. The flame resistant plastic as claimed in claim 1, which contains from 5 to 20% by weight of guanidine barbiturates or guanidine thiobarbiturates or their mixtures.

5. The flame resistant plastic as claimed in claim 1, at least 95% by weight of the guanidine barbiturates or guanidine thiobarbiturates having a maximum grain size of 0.025 mm.

6. The flame resistant plastic as claimed in claim 1, which additionally contains further flame retardants.

7. A process for enhancing the flame resistance of plastics, in which guanidine barbiturates or guanidine thiobarbiturates or their mixtures are added as flame retardants to the plastics or to materials employed to form the plastics.

8. A method of rendering plastics flame retardant, which comprises incorporating a flame retardant amount of guanidine barbiturates or guanidine thiobarbiturates in the plastics or to materials employed to form the plastics.

9. Guanidine barbiturate and guanidine thio-barbiturate.

* * * * *